(12) United States Patent
Nicolaides et al.

(10) Patent No.: US 10,533,954 B2
(45) Date of Patent: Jan. 14, 2020

(54) APPARATUS AND METHODS FOR COMBINED BRIGHTFIELD, DARKFIELD, AND PHOTOTHERMAL INSPECTION

(71) Applicant: KLA-Tencor Corporation, Milpitas, CA (US)

(72) Inventors: Lena Nicolaides, Castro Valley, CA (US); Mohan Mahadevan, Santa Clara, CA (US); Alex Salnik, San Bruno, CA (US); Scott A. Young, Soquel, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 167 days.

(21) Appl. No.: 15/692,863

(22) Filed: Aug. 31, 2017

(65) Prior Publication Data

US 2018/0003648 A1  Jan. 4, 2018

Related U.S. Application Data

(62) Division of application No. 14/618,586, filed on Feb. 10, 2015, now Pat. No. 9,772,297.
(Continued)

(51) Int. Cl.
*G01N 21/00* (2006.01)
*G01N 21/95* (2006.01)
(Continued)

(52) U.S. Cl.
CPC ..... *G01N 21/9505* (2013.01); *G01N 21/1717* (2013.01); *G01N 21/9501* (2013.01);
(Continued)

(58) Field of Classification Search
CPC ............... G01N 21/9505; G01N 21/01; G01N 2021/8822; G01N 2021/8825
(Continued)

(56) References Cited

U.S. PATENT DOCUMENTS

| 4,407,008 A | 9/1983 | Schmidt et al. |
| 4,750,822 A | 6/1988 | Rosencwaig et al. |

(Continued)

FOREIGN PATENT DOCUMENTS

| CN | 1662808 A | 8/2005 |
| EP | 0930498 A2 | 7/1999 |

OTHER PUBLICATIONS

Chinese Office Action and Search Report, dated Aug. 16, 2018, Application No. 201580008360.9. English Translation included. 19 Pages.

(Continued)

*Primary Examiner* — Sunghee Y Gray
(74) *Attorney, Agent, or Firm* — Kwan & Olynick LLP

(57) ABSTRACT

Disclosed are methods and apparatus for detecting defects or reviewing defects in a semiconductor sample. The system has a brightfield (BF) module for directing a BF illumination beam onto a sample and detecting an output beam reflected from the sample in response to the BF illumination beam. The system has a modulated optical reflectance (MOR) module for directing a pump and probe beam to the sample and detecting a MOR output beam from the probe spot in response to the pump beam and the probe beam. The system includes a processor for analyzing the BF output beam from a plurality of BF spots to detect defects on a surface or near the surface of the sample and analyzing the MOR output beam from a plurality of probe spots to detect defects that are below the surface of the sample.

9 Claims, 5 Drawing Sheets

Related U.S. Application Data

(60) Provisional application No. 61/939,135, filed on Feb. 12, 2014.

(51) Int. Cl.
*G01N 21/17* (2006.01)
*G01N 21/88* (2006.01)

(52) U.S. Cl.
CPC ............... *G01N 2021/8825* (2013.01); *G01N 2201/06113* (2013.01)

(58) Field of Classification Search
USPC ............................... 356/600, 237.1; 702/35
See application file for complete search history.

(56) References Cited

U.S. PATENT DOCUMENTS

| | | | |
|---|---|---|---|
| 4,795,260 A | 1/1989 | Schuur et al. | |
| 5,058,982 A | 10/1991 | Katzir | |
| 5,074,669 A | 12/1991 | Opsal | |
| 5,248,876 A | 9/1993 | Kerstens et al. | |
| 5,781,294 A | 7/1998 | Nakata et al. | |
| 6,248,988 B1 | 6/2001 | Krantz | |
| 6,288,780 B1 | 9/2001 | Fairley et al. | |
| 6,429,897 B2 | 8/2002 | Derndinger et al. | |
| 6,552,803 B1 | 4/2003 | Wang et al. | |
| 6,654,109 B2 | 11/2003 | Li et al. | |
| 6,674,572 B1 | 1/2004 | Scheruebl et al. | |
| 6,867,406 B1 | 3/2005 | Fairley et al. | |
| 6,891,627 B1 | 5/2005 | Levy et al. | |
| 6,934,019 B2 | 8/2005 | Geffen et al. | |
| 6,963,401 B2 | 11/2005 | Opsal et al. | |
| 7,075,058 B2 | 7/2006 | Chinn et al. | |
| 7,106,446 B2 | 9/2006 | Nicolaides et al. | |
| 7,109,458 B2 | 9/2006 | Fairley et al. | |
| 7,259,869 B2 | 8/2007 | Hwang et al. | |
| 7,399,950 B2 | 7/2008 | Fairley et al. | |
| 7,460,219 B2 | 12/2008 | Jung et al. | |
| 7,724,362 B1 | 5/2010 | Rosengaus | |
| 7,782,452 B2 | 8/2010 | Mehanian et al. | |
| 8,312,772 B2 | 11/2012 | Tas et al. | |
| 8,451,440 B2 | 5/2013 | Hahn et al. | |
| 8,576,393 B2 | 11/2013 | Gutman | |
| 8,634,070 B2* | 1/2014 | Ishihara | G01N 21/95 356/237.1 |
| 8,848,185 B2 | 9/2014 | Barak et al. | |
| 8,885,918 B2 | 11/2014 | Amanullah et al. | |
| 9,772,297 B2 | 9/2017 | Nicolaides et al. | |
| 2002/0054291 A1 | 5/2002 | Tsai et al. | |
| 2003/0137664 A1 | 7/2003 | Opsal et al. | |
| 2003/0234933 A1 | 12/2003 | Nicolaides et al. | |
| 2004/0051976 A1 | 3/2004 | Karin et al. | |
| 2004/0075879 A1 | 4/2004 | Karin | |
| 2004/0140417 A1 | 7/2004 | Karin | |
| 2005/0036136 A1 | 2/2005 | Opsal et al. | |
| 2005/0089763 A1 | 4/2005 | Tan et al. | |
| 2005/0111082 A1 | 5/2005 | Karin | |
| 2005/0214956 A1 | 9/2005 | Li et al. | |
| 2006/0007434 A1 | 1/2006 | Furman et al. | |
| 2007/0057184 A1* | 3/2007 | Uto | G01N 21/95607 250/310 |
| 2007/0121106 A1 | 5/2007 | Shibata et al. | |
| 2008/0036998 A1 | 2/2008 | Salnik et al. | |
| 2008/0231845 A1 | 9/2008 | Grossman et al. | |
| 2009/0059215 A1 | 3/2009 | Mehanian et al. | |
| 2010/0295938 A1 | 11/2010 | Hahn et al. | |
| 2010/0315625 A1 | 12/2010 | Salnik et al. | |
| 2010/0328670 A1 | 12/2010 | Rotter et al. | |
| 2012/0013899 A1 | 1/2012 | Amanullah | |
| 2013/0314710 A1 | 11/2013 | Levy et al. | |
| 2014/0158883 A1 | 6/2014 | Zewail | |
| 2015/0226676 A1 | 8/2015 | Nicolaides et al. | |

OTHER PUBLICATIONS

"U.S. Appl. No. 14/618,586, Non Final Office Action dated Dec. 1, 2016", 10 pages.
"U.S. Appl. No. 14/618,586, Notice of Allowance dated May 25, 2017", 8 pages.
"U.S. Appl. No. 14/618,586, Restriction Requirement dated Sep. 22, 2016", 10 pages.
"European Application Serial No. 15749379.2, European Search Report dated Aug. 1, 2017", 7 pages.
"IMEC and PVA Tepla Report Breakthrough Results in TSV Void Detection in 3D Stacked IC Technology", Jan. 17, 2013, 1 pg.
"Inspection and Metrology on a Common Platform for Advanced Packaging in HVM", SEMATECH Workshop on 3D Interconnect Metrology, Jul. 2013, 24 pgs.
"Int'l Application Serial No. PCT/US2015/015471, Search Report dated May 19, 2015", 3 pgs.
Chin, Harrison H. , "Wafer Inspection Based on Photothermal Effects", Applied Concept Research, Inc., Retrieved from the Internet: < http://www.appliedconceptresearch.com/Wafer%20Inspection%20Based%20on%20Photothermal%20Effect.pdf >, Accessed on Jan. 22, 2014, 3 pgs.
Czurratis, Peter et al., "New Scanning Acoustic Microscopy Technologies Applied to 3D Integration Applications", SEMATECH Workshop on 3D interconnect Metrology, 2013, 16 pgs.
Kwon, Ohmyoung et al., "Scanning Thermal Wave Microscopy (STWM)", Transactions of the ASME, vol. 125, Feb. 2003, pp. 156-163.
Opsal, Jon et al., "Thermal-wave detection and thin-film thickness measurements with laser beam deflection", Applied Optics, vol. 22, No. 20, Oct. 1983, pp. 3169-3179.
Rosencwaig, Allan , "Thermal Wave Monitoring and Imaging of Electronic Materials and Devices", Therma-Wave, Inc., 1994, pp. 74-109.

* cited by examiner

APPARATUS AND METHODS FOR COMBINED BRIGHTFIELD, DARKFIELD, AND PHOTOTHERMAL INSPECTION

CROSS-REFERENCE TO RELATED APPLICATION

This application is a divisional of U.S. patent application Ser. No. 14/618,586, filed 10 Feb. 2015, which claims priority to U.S. Provisional Patent Application No. 61/939,135, filed 12 Feb. 2014, which applications are incorporated herein by reference in their entirety for all purposes.

TECHNICAL FIELD OF THE INVENTION

The invention generally relates to the field of wafer and reticle inspection systems. More particularly the present invention relates to inspection and review of surface and sub-surface structures or defects.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device is fault free prior to shipment to the end users or customers.

There is a continuing need for improved semiconductor wafer inspection apparatus and techniques.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

A system for detecting defects or reviewing defects in a semiconductor sample are disclosed. The system includes a brightfield (BF) module for directing a BF illumination beam on a BF spot on a sample and detecting an output beam reflected from the BF spot on the sample in response to the BF illumination beam being directed on the BF spot and a modulated optical reflectance (MOR) module for directing a pump beam to a pump spot on the sample, directing a probe beam to a probe spot on the sample, and detecting a MOR output beam from the probe spot in response to the pump beam and the probe beam, wherein the probe spot is coincident with the pump spot. The system also includes a processor that is operable to perform or cause the following operations: (i) causing the BF module to scan the BF illumination beam on a plurality of BF spots on the sample and detect an output beam from the plurality of BF spots, (ii) causing the MOR module to scan the pump and probe beam on a plurality of pump and probe spots, respectively, and to detect a MOR output beam from the plurality of probe spots, (iii) analyzing the BF output beam from the plurality of BF spots to detect one or more defects on a surface or near the surface of the sample, and (iv) analyzing the MOR output beam from the plurality of probe spots to detect one or more defects that are below the surface of the sample.

In a specific implementation, the BF module and the MOR module share an objective. In another aspect, the system includes a darkfield (DF) module for directing a DF illumination beam on a DF spot on the sample and detecting an output beam scattered from the DF spot on the sample in response to the DF illumination beam being directed on the DF spot. In a further aspect, the processor is configured to cause the BF and DF illumination beam to scan the sample prior to scanning the pump and probe beam and determine one or more target locations for scanning the pump and probe beam based on analyzing the BF and DF output beam after the entire sample or a portion of the sample is scanned by the BF and DF illumination beam. In yet another aspect, the BF and DF module share a light source for generating the BF and DF illumination beam. In another implementation, the BF module has a BF light source for generating the BF illumination beam and the DF module has a DF light source for generating the DF illumination beam.

In a specific implementation, the MOR module comprises a pump laser source for generating the pump beam at a wavelength range between about 400 and 600 nm, a modulator for configuring the pump laser source to modulate the pump beam, a probe continuous wave (CW) laser source for generating the probe beam at a wavelength range between about 600 and 800 nm, illumination optics for directing the pump beam and probe beam towards the sample, a photothermal detector, and collection optics for directing the MOR output beam towards the photothermal detector for detecting the MOR output beam and generating an output signal that is filtered to isolate changes that are synchronous with modulation of the pump beam. In a further aspect, the BF module comprises a BF light source for generating the BF illumination beam, illumination optics for directing the BF illumination beam towards the sample, a BF detector, and collection optics for directing the BF output beam towards the BF detector for detecting the BF output beam. In a further aspect, the illumination optics of the BF module share one or more components with the illumination optics of the MOR module and the collection optics of the BF module share one or more components with the collection optics of the MOR module.

In a specific embodiment, the defects that are below the surface include one or more voids and/or changes in density of a material and/or changes in a sidewall angle and/or are within one or more through-silicon via (TSV) structure. In another aspect, the system includes an autofocus module for directing an autofocus beam towards the sample and detecting a reflected beam from the sample in response to the autofocus beam, and adjusting a focus of the system. In one aspect, the BF module, the MOR module, and the autofocus module share an objective. In another embodiment, the processor is configured to cause the BF illumination beam, pump, and probe beam to scan simultaneously. In another aspect, the BF module and MOR module share a same detector for detecting the BF output beam and the MOR output beam.

In an alternative embodiment, the invention pertains to a method of detecting defects or reviewing defects in a semiconductor sample, and the method includes (i) scanning a sample portion with a brightfield (BF) illumination beam, (ii) detecting a BF output beam reflected from the sample portion as the BF beam scans over the sample portion, (iii) determining surface or near-surface characteristics of the sample portion based on the detected BF output beam, (iv) finding candidate locations within the sample portion that are likely to have additional defects below a surface of the sample based on the determined surface or near-surface characteristics of the sample portion that were determined based on the detected BF output beam, (v) directing a modulated pump beam and a probe beam at each candidate location, (vi) detecting a modulated optical reflectivity signal from each candidate location in response to each probe beam being directed to each candidate location, and (vii) determining a feature characteristic that is below the surface at each candidate location based on the modulated optical reflectivity signal detected from such candidate location.

In a further aspect, the method includes (viii) detecting a darkfield (DF) output beam scattered from the sample portion as the BF beam scans over the sample portion or in response to scanning a darkfield beam over the sample portion, (ix) determining surface or near-surface characteristics of the sample portion based on the detected DF output beam, (x) finding a second plurality of candidate locations based on the surface or near-surface characteristics of the sample portion based on the detected DF output beam, (xi) detecting a modulated optical reflectivity signal from each second candidate location in response to each probe beam being directed to each second candidate location, and (xii) determining a feature characteristic that is below the surface at each second candidate location based on the modulated optical reflectivity signal detected from such second candidate location. In a further aspect, the first and second candidate locations are found by correlating surface or near-surface characteristics with a presence of sub-surface defects. In yet a further aspect, the first and second candidate locations are each associated with a sub-area of the sample portion that has one or more surface or near-surface characteristics that deviate by a predefined amount from an average of the sample portion. In yet another aspect, at least one of the first and second candidate locations has through-silicon vias (TSV's).

In another embodiment, the first and second candidate locations are selected to be distributed across its associated sub-area. In another example, the method includes determining whether the surface or near-surface characteristics indicate a presence of oxidation on the surface and removing the oxidation prior to directing the modulated pump beam and the probe beam at each candidate location. In another example, at least some of the candidate locations are each selected to be centered on a structure based on an image of such structure that is generated based on the BF output beam. In another implementation, at least some of the candidate locations are further selected to be distributed across a structure based on an image of such structure that is generated based on the BF output beam.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

In general, certain embodiments of the present invention pertain to a combination system having channels for brightfield (BF), darkfield (DF), and modulated optical reflectance (MOR). A combined apparatus is especially useful in detection and metrology of sub-surface defects, such as voids and other deformities in Cu-filled through Silicon via (TSV) structures or other 3D stacked semiconductor structures, as well as detection and metrology of surface characteristics and defects, in various structures on semiconductor samples, such as wafers.

Figure 1A:
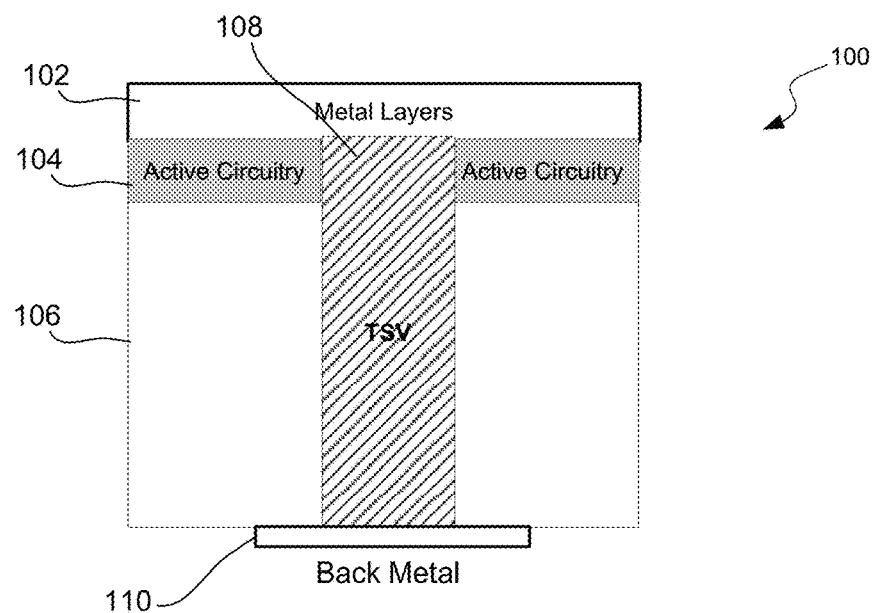
FIG. 1A is a diagrammatic side view of a Cu-filled through Silicon via (TSV).

FIG. 1A is a diagrammatic side view of a Cu-filled through Silicon via (TSV) structure 100. As shown, a Cu-filled TSV 108 is formed through Silicon bulk 106, as well as active circuitry area 104 so as to electrically couple a back metal portion 110 and one or more top metal layers 102.

Figure 1B:
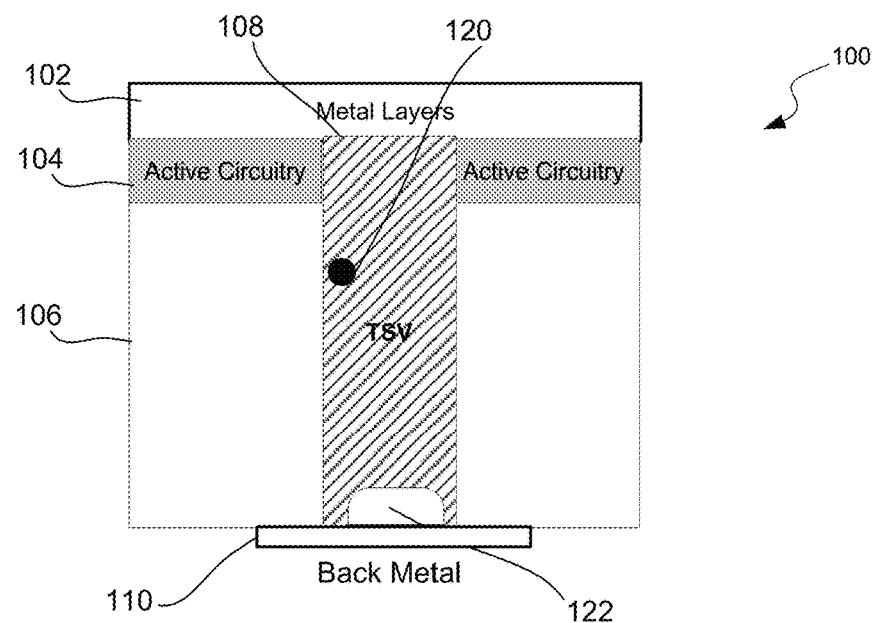
FIG. 1B is a diagrammatic side view of a Cu-filled through Silicon via (TSV) having sub-surface defects.

BF- and DF-based technologies can detect surface and near-subsurface defects in various structures (e.g., in active circuitry area 104) in various stages of the semiconductor manufacturing. However, certain features in integrated circuit (IC) manufacturing such as Cu-filled TSVs, may be located much deeper in the semiconductor structure than the sensitivity depth of conventional optical-based macro inspection techniques. FIG. 1B is a diagrammatic side view of a Cu-filled through Silicon via (TSV) having deep defects, such as void area 122 and particle defect 120.

In contrast to BF- or DF-based technology, MOR-based technology can be very sensitive to sub-surface features, such as defects located in TSV structures and defects located in the bulk of the material. Therefore, a combination of these optical and photothermal technologies into a single apparatus is expected to provide a tool capable of detecting defect signatures throughout the entire range of interest (e.g., from <1 um to >50 um below the surface). Another advantage of such a combined approach lies in its simplicity. Unlike X-rays or ultrasonic wavelengths, a photo-thermal system is straightforward to build, maintain, and use.

Figure 2:
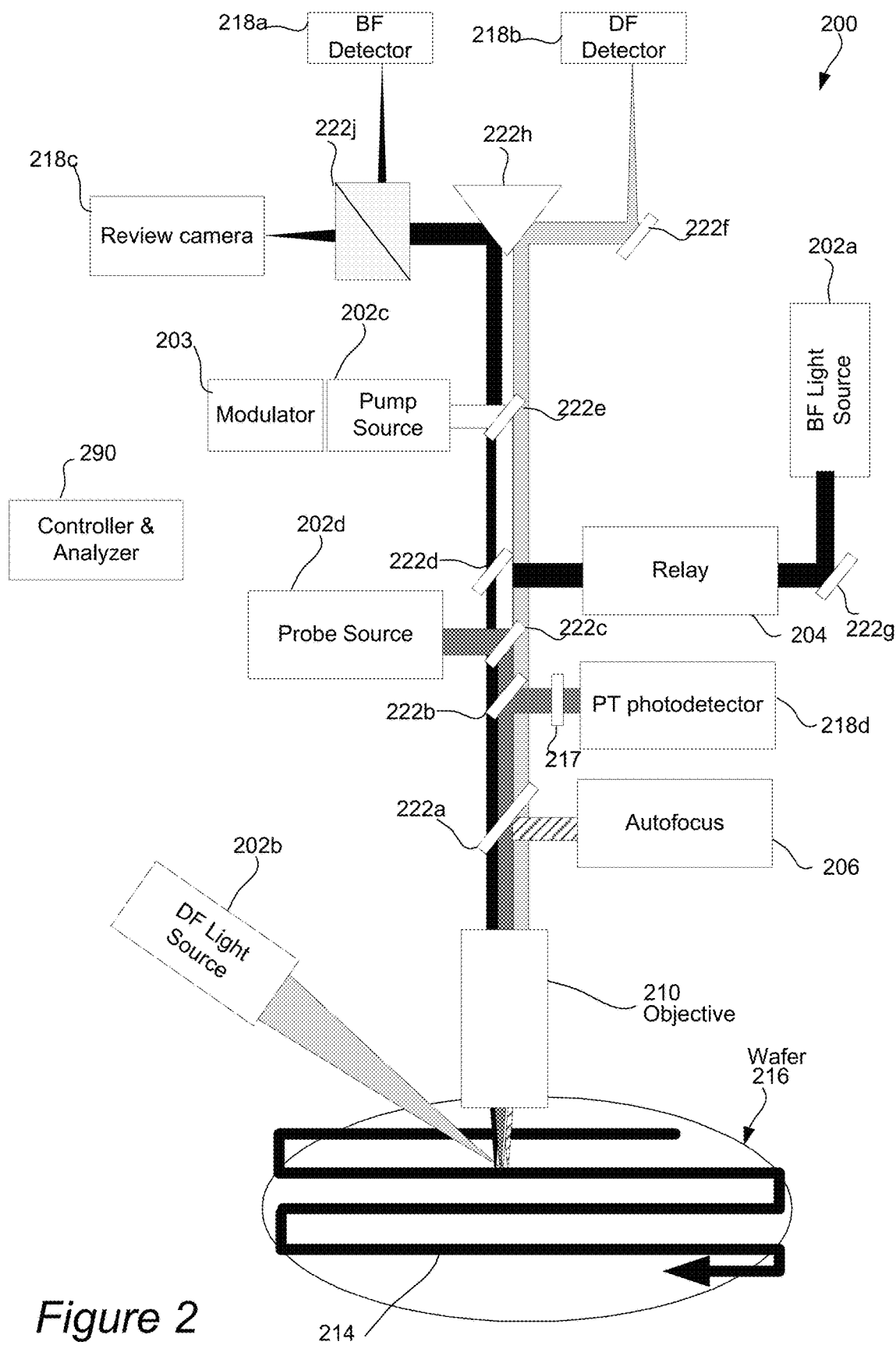
FIG. 2 is a schematic representation of a combined brightfield (BF), darkfield (DF), and modulated optical reflectance (MOR) apparatus in accordance with one embodiment of the present invention.

FIG. 2 is a schematic representation of a combined apparatus 200 in accordance with one embodiment of the present invention. The different illumination and output beams of the system 200 are illustrated as having different optical paths so as to simplify the drawing and more clearly show all the beams. The system 200 includes a photothermal MOR-based module and BF and DF based modules. The MOR, BF, and/or DF modules may share any one or more components or be completely separate modules. In the illustrated embodiment, the MOR and BF modules share some of the same illumination optics, such as objective 210. BF light source generates an illumination beam (black), which is directed towards the sample, e.g., wafer 216, via mirror 222g, relay 204, mirror 222d, and objective 210. Likewise, pump source 202c generates a pump beam of radiation (white), which is directed towards sample 216 via mirror 222e and focused onto the sample by the same objective 210. Probe source 202d also generates a probe beam, which is directed towards sample 216 via mirror 222c and focused onto the sample 216 by the same objective 210. Any of the illumination beams from any of the light sources described herein may also pass through a number of lenses which serve to relay (e.g., shape, focus or adjust focus offset, filter/select wavelengths, filter/select polarization states, resize, magnify, reduce distortion, etc.) the beam towards the sample 216.

The sample 216 may also be placed on a stage (not labeled) of the inspection system 200, and the inspection system 200 may also include a positioning mechanism for moving the stage (and sample) relative to the incident beams. By way of examples, one or more motor mechanisms may each be formed from a screw drive and stepper motor, linear drive with feedback position, or band actuator and stepper motor. The sample 216 may be any suitable patterned or unpatterned substrate, such a patterned or unpatterned silicon wafer.

In general, each optical element of the inspection system or module may be optimized for the wavelength range of the light for detecting defects or characterizing features of the sample 216. Optimization may include minimizing wavelength-dependent aberrations, for example, by selection of glass type, arrangement, shapes, and coatings (e.g., anti-reflective coatings, highly reflective coatings) for minimizing aberrations for the corresponding wavelength range. For example, the system optical elements may be arranged to minimize the effects caused by dispersion by wavelength ranges used by the BF and DF.

Any suitable BF source 202a may be used. Examples of BF light sources include a coherent laser light source, laser-driven light source, (e.g., deep UV or gas laser generator), a high-power plasma light source, a transillumination light source (e.g., halogen lamp), a filtered lamp, LED light source, etc. The inspection system may include any suitable number and type of light sources.

The BF source 202a may generate any suitable broadband radiation at any suitable incident angle, besides the illustrated normal angle. For instance, the BF illumination beam may be directed towards the sample 216 at an oblique angle. The location at which the BF source is directed to on the sample may be referred to as a BF spot. The BF spot may be between about 0.5 μm to about 5 μm. In one example, the BF spot is about 1 μm.

After the incident beam from light source 202a impinge on the sample 216, the light may then be reflected (and/or transmitted) and scattered from the sample 216, which is referred to herein as "output light" or an "output beam." The inspection system also includes any suitable lens arrangements for directing the output light towards one or more detectors. The corresponding BF output beam is collected from the sample in response to such BF illumination beam. As shown, the normal output beam (black) is collected along the normal axis, through objective 210, mirrors 222a, 222b, 222c, 222d, 222e, and reflected off optical element 222h, split by beam splitter 222j to impinge on both BF detector 218a and review camera 218c. By way of example, the BF detector 218a may be in the form of a CCD (charge coupled device) or TDI (time delay integration) detector, photomultiplier tube (PMT), and other sensor.

The system 200 may also include a DF channel comprising a DF light source 202b for generating a DF illumination beam (gray) towards sample 216 at a particular angle, such as the illustrated oblique angle. The location at which the DF source is directed to on the sample may be referred to as a DF spot. The DF spot may be between about 0.5 μm to about 10 μm, or more specifically between 0.5 μm and 5 μm. In one example, the DF spot is about 1 μm. The DF spot may be coincident with the BF spot, and both the BF and DF spots may be generated simultaneously. Alternatively, the BF and DF beams may be simultaneously directed towards different spots on the sample. One example system that includes simultaneous BF and DF inspection is the Altair 8900 available from KLA-Tencor Corp. of Milpitas, Calif.

The DF collection channel may be configured to collect scattered output light (gray) from the sample 216 in response to the incident DF beam. As shown, scattered DF output light may be collected through objective 210, mirrors 222a, 222b, 222c, 22d, 222e, and reflected off optical element 222h and mirror 222f to be directed DF detector 218b.

The system 200 may also include a controller and analyzer 290 for analyzing the output data from the BF and DF modules as described further below.

The system 200 also includes a MOR-based module. The pump source 202c generates an intensity-modulated pump beam of radiation. For example, the light source may include an intensity-modulated laser or incoherent light source. A gas, solid state, or semiconductor laser may be utilized, including a laser system coupled with an optical fiber. The pump source may generate a pump beam having any suitable wavelength range. For instance, the pump beam has a wavelength range that is low enough to have strong absorption by the sample (e.g., silicon) while keeping within the bandwidth requirements of the shared illumination optics of the BF channel. In a specific implementation, the pump beam has a stable wavelength range that is between about 400 to 600 nm. A broadband tunable source may be used to achieve various wavelengths. A spectroscopic pump source may be used to achieve better reflectivity from the sample.

The pump beam is intensity modulated. The pump beam may be configured to modulate the pump beam at a predefined frequency or to vary the modulation frequency to obtain additional data at a plurality of modulation frequencies. Accordingly, the pump source will typically include a modulator 203 that supplies a drive signal to the pump source for modulating the intensity of the pump beam. The modulation frequency can vary from a few Hertz (Hz) to tens of MHz. In one implementation, the modulation frequency has a range between about 10 Hz and 10 MHz, such as 1 MHz, which will create plasma waves in a typical semiconductor sample.

As the pump beam source 202c is switched on, the pump beam may be projected onto the surface of the sample causing localized heating of the sample 216. As the pump source is modulated, the localized heating (excitation) and subsequent cooling (relaxation) may create a train of thermal and plasma waves within the sample 216. The thermal and plasma waves may reflect and scatter off various features and interact with various regions within the sample 216 such that the flow of heat and/or plasma from the pump beam spot may be altered. In an alternative implementation, the entire wafer may be relaxed in a special chamber and/or in a special environment utilizing temperature treatment.

Plasma waves are only generated in semiconductor materials and generally not in conductive materials, such as copper, while thermal waves are generated in both semiconductor and conductive materials. Plasma and thermal waves propagate from the area of creation (e.g., the pump spot on the surface) to away from the surface. Plasma and thermal waves tend to be generated where the material's absorption coefficient is high, such as a silicon material, and reflect off any imperfections of the crystalline structure or depend on particular structure characteristics. Imperfections or feature characteristics, which may affect plasma or thermal waves, may include voids, particles, missing or added material, changes in sidewall angle, a sidewall's deviation from vertical, density changes in material, etc. Thermal waves can penetrate quite deep, and the depth of penetration can be changed by altering the intensity modulation frequency of the pump laser.

The thermal and plasma waves and their interactions with the underlying structures or defects and their different absorption coefficients or thermal contrast will have a direct effect on the reflectivity at the surface. That is, features and regions below the sample surface that alter the passage of the thermal and plasma waves will alter the optical reflective patterns at the sample surface. Thermal contrast generally depends on differences in thermal conductivity multiplied by volume or differences in thermal diffusivity. If there is thermal contrast between defects and surrounding non-defective structures or field, significant changes of surface reflectivity can occur.

By monitoring the changes in reflectivity of the sample at the surface, information about characteristics below the surface may be investigated. For detection of defects, the MOR-based module includes a mechanism for monitoring changes in reflectivity caused by the underlying structures and/or defects. The system 200 includes a probe beam source 202d that generates an unmodulated probe beam of radiation. For instance, the probe source 202d may be a CW (continuous wave) laser or a broadband or white light source. The probe source may generate a probe beam having any suitable wavelength range, depending on the reflectivity characteristics of the sample material. For instance, a probe beam that works well with copper has a wavelength range of about 600 to 800 nm. In another embodiment, the light source outputs illumination light at a range between about 700 nm and 950 nm (e.g., visible, IR, and/or NIR wavelength range) so as to penetrate a 3D stack memory device. Examples of light sources include a laser-driven light source, a high-power plasma light source, a transillumination light source (e.g., halogen or Xe lamp), a filtered lamp, LED light sources, etc. Multiple LED or speckle buster laser diodes are also possible sources.

The probe beam can be focused onto a probe spot that shares at least a portion of the same spot as the incident pump beam. That is, the probe beam impingement may be coincident with the pump spot. The system 200 may also include a scanning element, such as a deflector, to move the pump and probe beams together so as to scan a same area of the sample. At least one beam tracker (e.g., 222c or 222a) may be provided in the path of either the pump or probe beams for adjusting the relative positions of the pump and probe beams on the sample. The tracker can be used to vary the lateral offset of the pump and probe beams for obtaining multiple MOR measurements. The probe beam may be directed normal to the sample surface (as shown) or at any suitable angle of incidence. In another embodiment, the probe beam may be adjusted to a high power for flash annealing the sample 216.

The MOR channel may include a collection path for collecting output radiation reflected or scattered from the sample 216 in response to the pump and probe beams incident on the sample. For instance the collection path may include any suitable lens or optics elements (e.g., 217) for relaying and/or magnifying the output beam and directing it to a photothermal (PT) detector 218d.

The PT detector 218d is generally configured to monitor the changes in reflectivity of the probe beam reflected from the sample in response to the incident probe beam. The PT detector 218d senses the output radiation and generates an output signal that is proportional to the reflected power of the probe beam and is, therefore, indicative of the varying optical reflectivity of the sample surface. The PT detector 218d may be in any suitable form to detect MOR-based signals, such as integrated intensity signals. For example, the PT detector 218d may include one or more photodetector elements, such as a simple silicon photodiode or an array of photodiodes. The PT detector 218d preferably has low noise, high stability, and low cost.

The output signal from the PT detector 218d may be filtered to isolate the changes that are synchronous with the pump beam modulation frequency. For many implementations, filtering may be performed using a heterodyne or lock-in detection system. U.S. Pat. No. 5,978,074 describes several example lock-in detection systems, which patent is incorporated herein by reference in its entirety. A lock-in detector may also be used to measure both the in-phase (I) and quadrature (Q) components of the detector output. The two channels of the output signal, namely the amplitude $A^2=I^2+Q^2$ and phase $\theta=\arctan(I/Q)$ are conventionally referred to as the Modulated Optical Reflectance (MOR) or Thermal Wave (TW) signal amplitude and phase, respectively.

Controller or analyzer 290 may also be configured for analyzing the output from the PT photodetector 218d. In general, the phase and change of the reflectivity signal, as compared to the modulated pump signal, is monitored. Dynamics of the thermal- and carrier plasma-related components of the total MOR signal in a semiconductor is given by the following general equation:

$$\left( \frac{\partial R}{\partial T} + \frac{\partial R}{\partial N} \Delta N_0 \right)$$

where $\Delta T_0$ and $\Delta N_0$ are the temperature and the carrier plasma density at the surface of a semiconductor, R is the optical reflectance, $\delta R/\delta T$ is the temperature reflectance coefficient and $\delta R/\delta N$ is the carrier reflectance coefficient. For silicon, $\delta R/\delta T$ is positive in the visible and near-UV part of the spectrum while $\delta R/\delta N$ remains negative throughout the entire spectrum region of interest. The difference in sign results in destructive interference between the thermal and plasma waves and decreases the total MOR signal at certain conditions. The magnitude of this effect depends on the nature of a semiconductor sample and on the parameters of the photothermal system, especially on the pump and probe wavelengths.

The analyzer and processor 290 may also be communicatively coupled with one or more of the system components for controlling or sensing operating parameters. For instance, the process 290 may be configured to adjust and control modulation of the pump beam via modulator 203.

The system 200 may also include an autofocus module 206 for providing autofocus of the target sample. The autofocus generally generates an autofocus beam that is directed by mirror 222a through objective 210 towards the sample and then detects a response signal to determine and adjust focus. In this embodiment, the autofocus shares the same objective as the BF and MOR-based modules.

Figure 3:
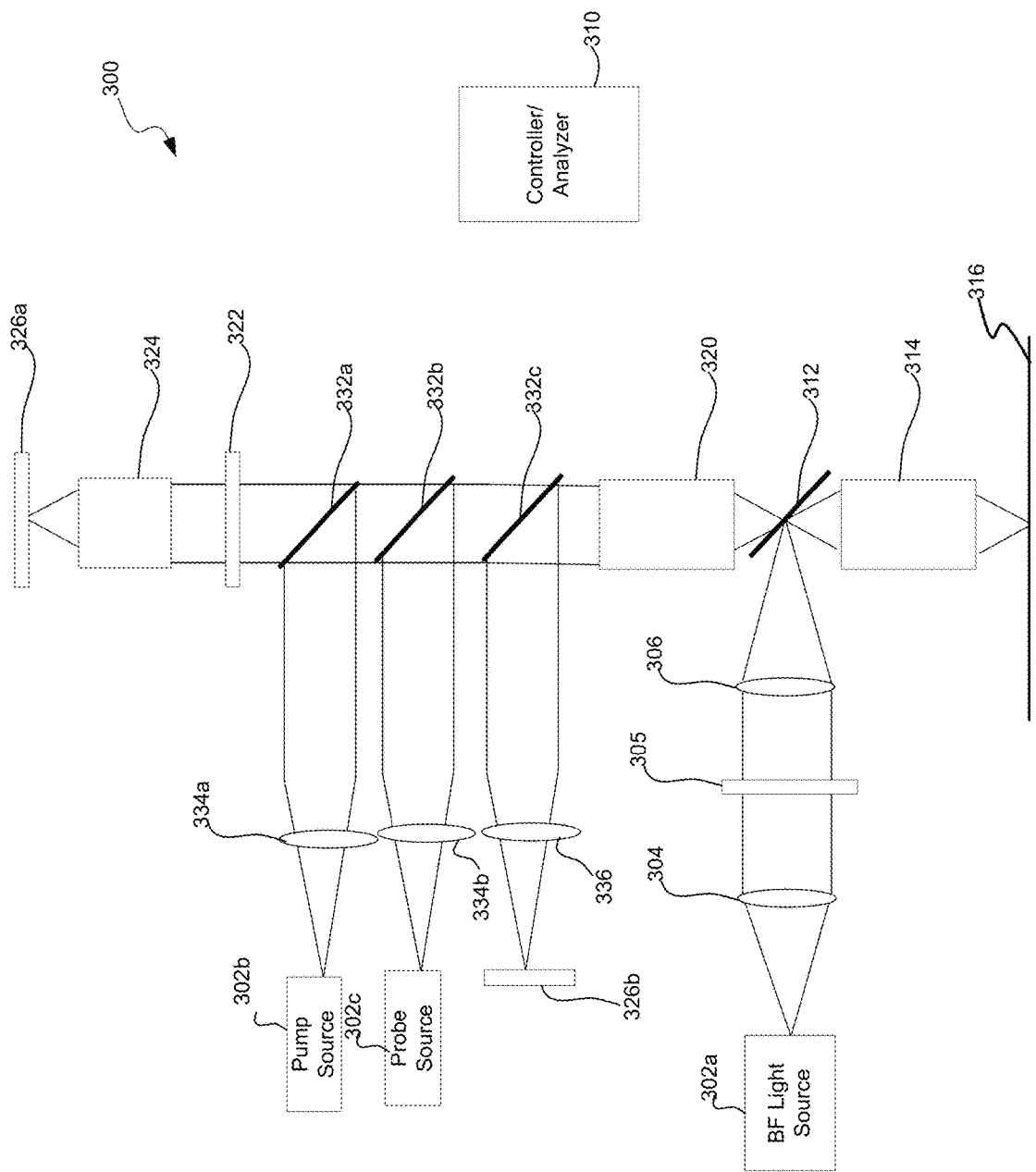
FIG. 3 is a diagrammatic representation of a combined BF and MOR inspection system in accordance with an alternative embodiment of the present invention.

FIG. 3 is a diagrammatic representation of an inspection system 300 in accordance with an alternative embodiment of the present invention. This system 300 may include one or more of the components described with respect to the system of FIG. 2. As shown in FIG. 3, the system may include a BF light source 302a for generating an incident beam, such as a broadband light source. Examples of light sources include a coherent laser light source, laser-driven light source, (e.g., deep UV or gas laser generator), a high-power plasma light source, a transillumination light source (e.g., halogen lamp), a filtered lamp, LED light source, etc. The inspection system may include any suitable number and type of light sources.

The incident beam from the BF light source 302a then passes through a number of lenses which serve to relay (e.g., shape, focus, resize, magnify, reduce distortion, etc.) the beam towards a sample 316. In the illustrated embodiment, the incident beam passes through lens 304, which collimates the incident beam, and then through lens 306, which converges the incident beam. The incident beam is then received by beam splitter 312 that then reflects the incident beam through objective lens 314, which focuses the incident beam onto sample 316 at one or more incident angles.

The inspection system 300 may also include an illumination selector 305 positioned at a pupil plane of the illumination beam from light source 302a. In one embodiment, the illumination selector 305 is in the form of a configurable pupil aperture that is adjustable to produce a plurality of different illumination beam profiles at the pupil plane. The inspection system 300 may also include one or more positioning mechanisms for selectively moving the different aperture configurations of the illumination selector into the path of the incident beam from light source 302a.

After the incident beam(s) from light source 302a impinge on the sample 316, the light may then be reflected (and/or transmitted) and scattered from the sample 316, which is referred to herein as "output light" or an "output beam." The inspection system also includes any suitable lens arrangements for directing the output light towards one or more detectors. In the illustrated embodiment, the output light passes through beam splitter 312, Fourier plane relay lens 320, imaging aperture 322, and zoom lens 324. The Fourier plane relay lens generally relays the Fourier plane of the sample to the imaging aperture 322. The imaging aperture 322 may be configured to block portions of the output beams. For instance, the aperture 322 is configured to pass all of the output light within the objective numerical aperture in a bright field inspection mode, and configured to pass only the scattered light from the sample during a dark field inspection mode. A filter may also be placed at the imaging aperture 322 to block higher orders of the output beams so as to filter periodic structures from the detected signal.

After going through the imaging aperture 322, the output beam may then pass through any number of optical elements, such as beam splitters 332a, 332b, and 332c, and then through zoom lens 324, which serves to magnify the image of the sample 316. The output beam then impinges upon detector 326a. By way of example, the detector may be in the form of a CCD (charge coupled device) or TDI (time delay integration) detector, photomultiplier tube (PMT), and other sensor.

The system 300 may also include a pump source 302b for generating a pump beam that is directed by one or more lens and optical elements (e.g., 334a, 332a~c, 320, 312, and 314) towards sample 316. Likewise, probe source 302c generates a probe beam that is directed towards the sample by one or more lens and optical elements (e.g., 334b, 332b, 332c, 320, 312, and 314) towards sample 316. An output beam from sample 316 is also directed towards PT detector 326b by one or more lens (e.g., 314, 312, 320, 332, and 336).

The signals captured by the sensors of the above described systems can be processed by a controller or analyzer system (290 or 310), which may include a signal processing device having an analog-to-digital converter configured to convert analog signals from the sensor into digital signals for processing. The controller may be configured to analyze intensity, phase, and/or other characteristics of the sensed light beam. The controller may be configured (e.g., with programming instructions) to provide a user interface (e.g., on a computer screen) for displaying resultant test images and other inspection characteristics as described further herein. The controller may also include one or more input devices (e.g., a keyboard, mouse, joystick) for providing user input, such as changing aperture configuration, viewing detection results data or images, setting up a inspection tool recipe. In certain embodiments, the controller is configured to carry out aperture selection or inspection techniques detailed below. Techniques of the present invention may be implemented in any suitable combination of hardware and/or software. The controller typically has one or more processors coupled to input/output ports, and one or more memories via appropriate buses or other communication mechanisms.

The controller may be any suitable combination of software and hardware and is generally configured to control various components of the inspection system. For instance, the controller may control selective activation of the illumination sources, modulation of the pump source, illumination selector/aperture settings, the imaging aperture settings, etc. The controller may also be configured to receive the image or signal generated by each detector and analyze the resulting image or signal to determine whether defects are present on the sample, characterize defects present on the sample, or otherwise characterize the sample. For example, the controller may include a processor, memory, and other computer peripherals that are programmed to implement instructions of the method embodiments of the present invention.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

It should be noted that the above description and drawings are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

A brightfield (BF) and darkfield (DF) module can detect defects that are either on the surface or covered by a very thin film. These modules can typically detect undersurface defects only when they are closer to the surface or they generate bumps in the stack that can propagate to the surface and, therefore, create a detectable surface defect. The MOR-based module can detect defects that are located deeper within sample, such as at the bottom or on a sidewall of a TSV structure.

BF/DF and MOR-based modules can be used simultaneously to detect defects or analyze characteristics on both the surface and deeper within the sample. Even for defects close to or on the surface, the BF/DF and MOR-based modules may be used together to enhance characterization of such defect. The BF/DF and MOR-based inspections may result in different defects or characteristics for a same location. Analysis techniques for finding defects and obtaining feature characteristics are further described below. In general, the BF/DF and MOR-based modules may be used to find defects that have different thermal and optical signatures.

In another embodiment, the BF/DF module and MOR-based modules can be used sequentially to enhance the inspection process. Although not required, the BF or DF modules may share a detector with the MOR-based modules since such modules are not used at the same time.

Figure 4:
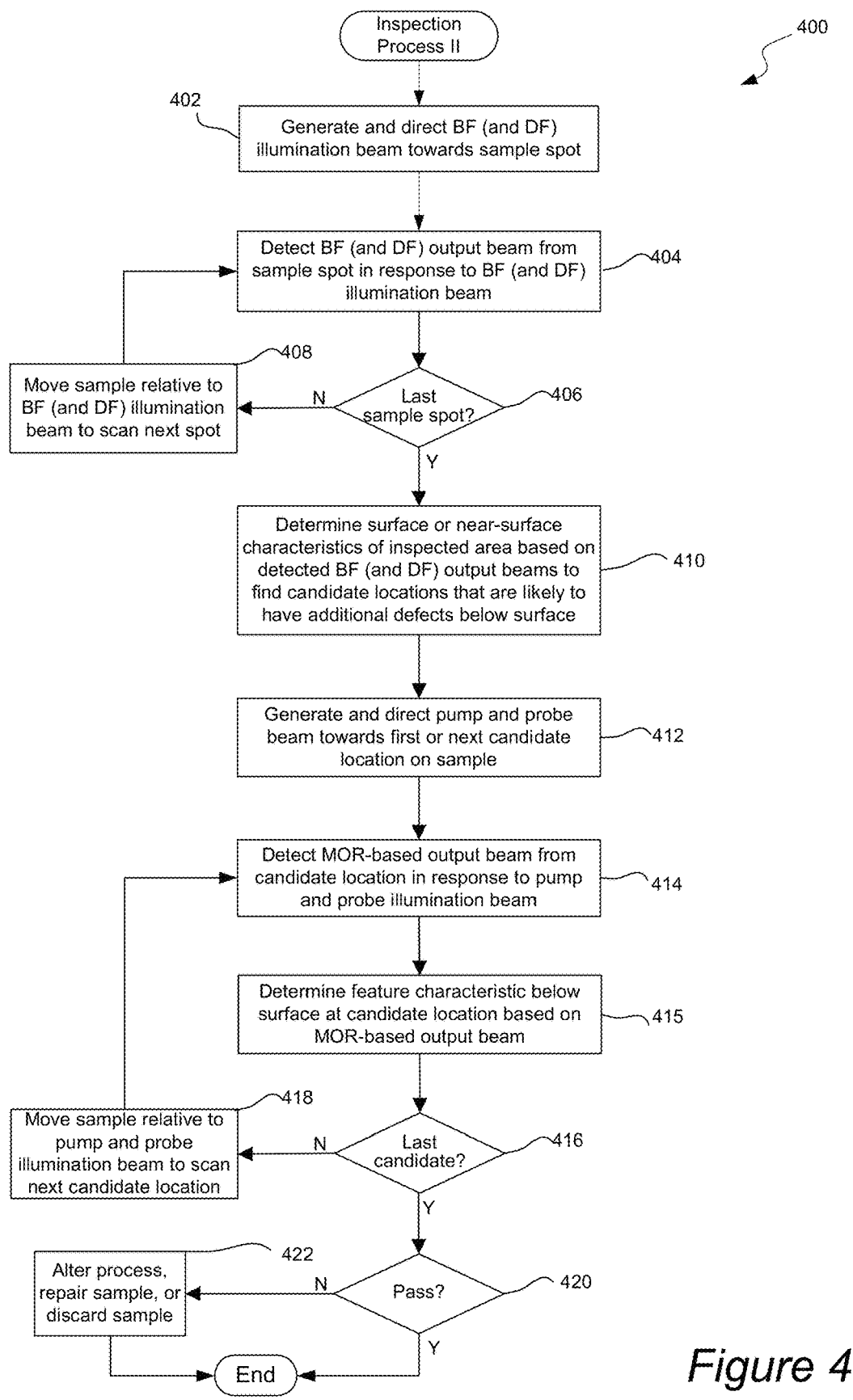
FIG. 4 is a flowchart illustrating an inspection procedure in accordance with one embodiment of the present invention.

FIG. 4 is a flowchart illustrating an inspection procedure 400 in accordance with one embodiment of the present invention. As shown, a BF is initially generated and directed towards a sample spot in operation 402. Optionally, a DF illumination beam may also be directed towards such initial sample spot. A BF (and DF) output beam may then be detected from the sample spot in response to the BF (and DF) illumination beam in operation 404. BF and DF output data, such as detected signals or images, may be simultaneously collected.

It may then be determined whether the last spot has been reached in operation 406. For instance, it is determined whether the entire area to be inspected has been scanned by the BF (and optionally DF) beam. The entire sample or a portion of the sample may be scanned with the BF (and DF) beams. If the last sample spot has not yet been reached, the sample may then be moved relative to the BF (and DF) illumination beam to scan a next spot in operation 408.

The BF (and DF) beam may be scanned across individual swaths of the sample. For instance, the BF and DF beams are scanned across a first swath in a first scan direction. These BF and DF beams may then be scanned across another a second swath in a scan direction that is opposite to the first swath's scan direction so that a serpentine scan pattern is implemented. Alternatively, the BF and DF beams may be scanned across the sample with any suitable scan pattern, such as a circular or spiral scan pattern. Of course, the sensors may have to be arranged differently (e.g., in a circular pattern) and/or the sample may be moved differently (e.g., rotated) during scanning in order to scan a circular or spiral shape from the sample.

After the initial scan is completed, surface or near-surface characteristics of the inspected area may then be determined based on the detected BF (and DF) output beam to find candidate locations that are likely to have additional defects below the surface in operation 410. That is, candidate locations that may contain defects that are not on the surface or near the surface may be located by analysis of the BF (and DF) output data.

In one embodiment, die-to-die, cell-to-cell, or die-to-database comparisons are performed to locate differences that are above a particular threshold, and these differences may then be classified as specific defect types. Some of these defect types may be determined to correlate with deeper defects.

Different types of defects or characteristics can be seen by the BF and the DF channels. BF output data can generally be used to detect defects in the form of planar deformity of surface structures. For instance, some structures may appear larger or smaller than they are designed to be. The BF output data can also indicate changes in film thickness, for example, in the form of color changes. Color changes in the BF response can also be impacted by changes in the material itself (e.g., density changes). Additionally, groups of structures that have become defective (even if only individual structures within the group are defective) may affect the surrounding structures. In contrast, DF output data can detect particle defects and roughness on the surface, local gradients in structure height for a particular structure, etc.

Certain defect or sample characteristics types that are obtained from BF or DF output data may be used to find candidate locations for further MOR-based review. For instance, particular Cu-filled through Silicon via (TSV) or groups of TSV structures may have a difference in a particular defect type (e.g., deformation) or characteristic (e.g., color), as compared to other TSV structures. These TSV's may be selected as candidate for further review by the MOR-based module.

In another example, the process is monitored using an averaging BF/DF technique to area anomalies. Averages in defect size, count, or other characteristics obtained from the BF/DF channels may be monitored per areas of the sample. For instance, a particular area may have bigger planar structures than other areas with the same type of structures, such as TSV's. Areas that deviate by a predetermined threshold from the average or mean of the other sample area may be selected as candidates for deeper MOR-based review. Alternatively, a sampling of locations within a deviating area may be selected for further MOR-based review. For instance, a particular large area having a plurality of TSV structures may be determined to have bigger structures, which may or not include TSV structures. A sampling of the TSV structures or all of the TSV structures within this particular large area may then be selected for MOR-based review. In one embodiment, candidate TSV locations are selected to be distributed across the particular area.

A pump and probe beam (e.g., from the MOR-based module) may be generated and directed towards a first candidate location on the sample in operation 412. A MOR-based output beam from the candidate location may then be detected in response to the pump and probe illumination beam in operation 414. A modulated pump beam is directed to a pump spot at the first candidate location on the sample, and a probe beam is directed to at least a portion of such pump spot. The reflected signal from the probe beam is detected, for example, by a PT-detector as described above.

A feature characteristic below the surface at the candidate location may be determined based on the MOR-based output beam in operation 415. The reflectivity data obtained from the MOR-based module can be used to find defects or further characterize features that are located deep in the sample at the candidate locations. Deeper defects and feature characteristics that can be monitored, measured, or found using a MOR-based review may include voids, particles, missing or added material, changes in sidewall angle, a sidewall's deviation from vertical, density changes in a material, etc.

Training sets of known deep (or non-surface) characteristics and defects may be analyzed to determine their MOR-based output signal. Models may also be generated and trained to calculate particular characteristic values or defect types based on MOR-based reflectivity output data.

It may then be determined whether the last candidate has been reviewed in operation 416. If not, the sample can be moved relative to the pump and probe illumination beam to scan a next candidate location in operation 418. The MOR-based channel is used to collect MOR-based output data for each candidate location until the last candidate is reviewed.

After the last candidate location is reached, it may then be determined whether the sample passes in operation 420. For instance, it is determined whether the defects are yield-limiting defects or merely nuisance type defects. The BF, DF, and MOR-based defects and feature characteristics may all be analyzed to determine whether the sample passes. It may also be determined whether particular feature characteristics are out of specification. If the sample does not pass, the process may be altered; the sample may be repaired, or the sample may be discarded in operation 422. In one implementation, the sample is discarded and the process is altered. If the sample passes, the procedure 400 may end, and the sample may be used as a product or be further processed. After further processing, the sample may be again inspected.

Using the BF/DF channels in a first inspection pass to find candidate locations for further MOR-based review can result in a more efficient inspection process. The BF/DF scans are significantly faster than a MOR-based scan. That is, the sample can be quickly scanned using a BF and/or DF inspection process. Suspect candidate locations can then be reviewed again by a MOR-based channel. The data that is obtained from the MOR-based review can be added to the data from the BF and/or DF inspection so as to provide a richer analysis for monitoring feature characteristics or finding defects on the sample.

The MOR-based output data can be used to improve the sensitivity of the BF and DF output data. In a TSV example, the thermal diffusion length in Copper can be varied significantly by adjusting the pump beam modulation frequency. At the low modulation frequencies, the thermal diffusion length and the sensitivity region of the system can be as large as 50-100 um allowing characterization of deep voids in Cu TSV structures (40-60 um deep and 3-8 um wide).

The BF modules can also be used to determine whether the TSVs have oxidized prior to inspection with a MOR-based module. For instance, a sampling of TSV images may be reviewed to determine whether there is oxide present. The presence of oxide during a MOR-based probe of TSV structures may cause the oxide to be burned off by the pump laser and cause unreliable results. It may be beneficial to remove the oxide from such TSV structures or the like. If there is oxide present, the sample may be polished (or some other technique implemented) so as to remove oxide. The MOR-based inspection can then proceed.

Figure 5:
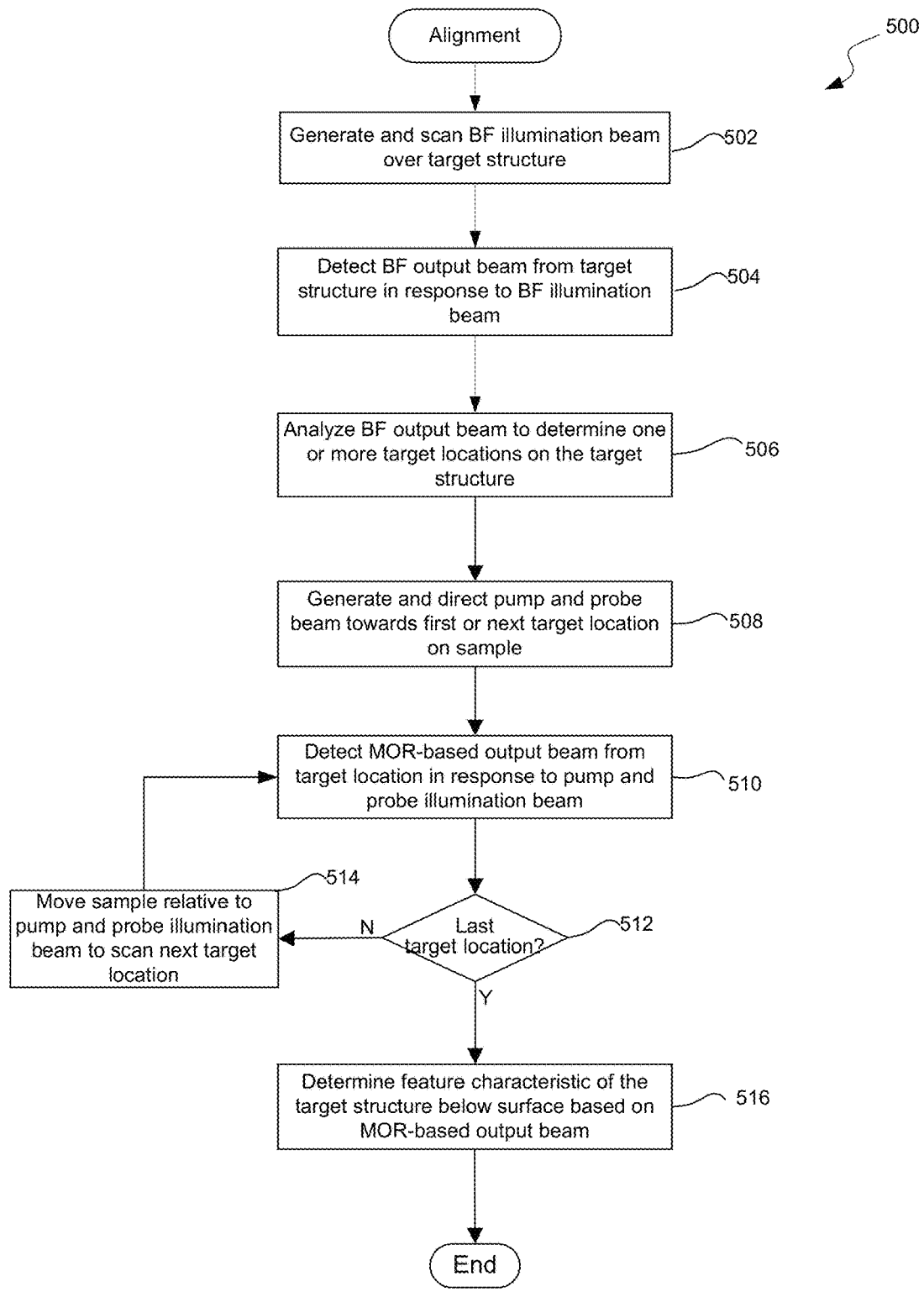
FIG. 5 is a flowchart illustrated a procedure for aligning MOR-based illumination beams in accordance with a specific implementation of the present invention.

The BF module may also be used to align the pump and probe beams with respect to a target structure. For instance, BF output data can be used to align the pump and probe beam so as to accurately probe one or more specific target locations of the target structure. In a specific example, the target structure is a TSV structure. FIG. 5 is a flowchart illustrated a procedure 500 for aligning MOR-based illumination beams in accordance with a specific implementation of the present invention. Initially, a BF illumination beam may be generated and scanned over a target structure in operation 502. A BF output beam may then be detected from the target structure in response to the BF illumination beam in operation 504. In one example, an image of the target structure may be generated based on the BF output beam.

The BF output beam may then be analyzed to determine one or more target locations on the scanned target structure in operation 506. In one embodiment, the edges of the target may be determined, and the center of the target may then be determined for MOR-based probing. For example, a line of pixels may be obtained across the width (or radius) of the target structure, and such line can be used to find the center of the target structure. Alternatively, two orthogonal directions of pixels may be obtained across the target structure to then locate a center of target structure.

If the target structure is large compared to the probe beam, a number of target locations may be selected to be distributed across the target structure so as to substantially cover the area of the target structure. In a distributed probing approach, a particular pattern of target locations may be chosen for systematically probing the target structure. In one example, a spiral pattern of locations that spiral out from the center of the structure is selected. In another example, a grid of locations that can be scanned in a serpentine pattern across the target is selected. In the TSV example, the TSV is probed so as to cover the entire TSV structure.

Once the one or more target locations are determined, a pump and probe beam may then be generated and directed towards a first target location on the sample in operation 508. A MOR-based output beam is then detected from the target location in response to the pump and probe illumination beam in operation 510. It may then be determined whether the last target location has been reached in operation 512. That is, it is determined whether the probe pattern is complete. If the last target location has not been reached, the sample may then be moved relative to the pump and probe illumination beam to scan the next target location in operation 514.

After the last target location is probed, a feature characteristic of the target structure that is below the surface may then be determined based on the MOR-based output beam in operation 516, as further described above. The alignment procedure 500 may be repeated on any number of target structures.

Although inspection systems and techniques for characterizing deep defects or features are described herein as being applied to certain types of TSV structures, it is understood that embodiments of the present invention may be applied to any suitable 3D or vertical semiconductor structures, such as NAND or NOR memory devices formed using terabit cell array transistors (TCAT), vertical-stacked array transistors (VSAT), bit cost scalable technology (BiCST), piped shaped BiCS technology (P-BiCS), etc. The vertical direction is generally a direction that is perpendicular to the substrate surface. Additionally, inspection embodiments may be applied at any point in the fabrication flow that results in multiple layers being formed on a substrate, and such layers may include any number and type of materials.

The optical layout of the inspection/review tools can vary from that described above. For example, the objective lens can be one of many possible layouts, as long as the transmission coatings are optimized for the particular selected wavelength band or sub-band and the aberration over each waveband is minimized. Any suitable lens arrangement may be used to direct each illumination beam towards the sample and direct the output beam emanating from the sample towards each detector. The illumination and collection optical elements of the system may be reflective or transmissive. The output beam may be reflected or scattered from the sample or transmitted through the sample.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of detecting defects or reviewing defects in a semiconductor sample, the method comprising:
    scanning a sample portion with a brightfield (BF) illumination beam;
    detecting a BF output beam reflected from the sample portion as the BF beam scans over the sample portion;
    determining surface or near-surface characteristics of the sample portion based on the detected BF output beam;
    finding candidate locations within the sample portion that are likely to have additional defects below a surface of the sample based on the determined surface or near-surface characteristics of the sample portion that were determined based on the detected BF output beam;
    directing a modulated pump beam and a probe beam at each candidate location;
    detecting a modulated optical reflectivity signal from each candidate location in response to each probe beam being directed to each candidate location; and
    determining a feature characteristic that is below the surface at each candidate location based on the modulated optical reflectivity signal detected from such candidate location.

2. The method of claim 1, further comprising:
    detecting a darkfield (DF) output beam scattered from the sample portion as the BF beam scans over the sample portion or in response to scanning a darkfield beam over the sample portion;
    determining surface or near-surface characteristics of the sample portion based on the detected DF output beam; and
    finding a second plurality of candidate locations based on the surface or near-surface characteristics of the sample portion based on the detected DF output beam;
    detecting a modulated optical reflectivity signal from each second candidate location in response to each probe beam being directed to each second candidate location; and
    determining a feature characteristic that is below the surface at each second candidate location based on the modulated optical reflectivity signal detected from such second candidate location.

3. The method of claim 2, wherein the first and second candidate locations are found by correlating surface or near-surface characteristics with a presence of sub-surface defects.

4. The method of claim 3 wherein the first and second candidate locations are each associated with a sub-area of the sample portion that has one or more surface or near-surface characteristics that deviate by a predefined amount from an average of the sample portion.

5. The method of claim 4, wherein at least one of the first and second candidate locations has through-silicon vias (TSV's).

6. The method of claim 4, wherein the first and second candidate locations are selected to be distributed across its associated sub-area.

7. The method of claim 1, further comprising:
    determining whether the surface or near-surface characteristics indicate a presence of oxidation on the surface; and
    removing the oxidation prior to directing the modulated pump beam and the probe beam at each candidate location.

8. The method of claim 1, wherein at least some of the candidate locations are each selected to be centered on a structure based on an image of such structure that is generated based on the BF output beam.

9. The method of claim 1, wherein at least some of the candidate locations are further selected to be distributed across a structure based on an image of such structure that is generated based on the BF output beam.

* * * * *